United States Patent
Banholzer et al.

(10) Patent No.: US 6,299,861 B1
(45) Date of Patent: Oct. 9, 2001

(54) IPRATROPIUM BROMIDE ENANTIOMER WITH PROLONGED DURATION OF EFFECT

(75) Inventors: Rolf Banholzer, Stuttgart; Richard Reichl, Gau-Algesheim; Bernd Disse, Mainz; Georg Speck, Ingelheim, all of (DE)

(73) Assignee: Boehringer Ingelheim KG, Ingelheim (DE)

(*) Notice: Subject to any disclaimer, the term of this patent is extended or adjusted under 35 U.S.C. 154(b) by 0 days.

(21) Appl. No.: 09/369,711

(22) Filed: Aug. 6, 1999

Related U.S. Application Data

(63) Continuation of application No. 08/983,420, filed as application No. PCT/EP96/03364 on Jul. 31, 1996, now abandoned.

(30) Foreign Application Priority Data

Aug. 1, 1995 (DE) ............................................. 195 28 145

(51) Int. Cl.[7] .............................. A61L 9/04; A61K 9/14; A61F 13/00
(52) U.S. Cl. ............................. 424/45; 424/46; 424/434; 424/489
(58) Field of Search ........................ 424/434, 45, 489, 424/46

(56) References Cited

U.S. PATENT DOCUMENTS

| | | | |
|---|---|---|---|
| 4,385,048 | * | 5/1983 | Mygind et al. .................... 424/45 |
| 5,225,183 | * | 7/1993 | Purewal et al. .................... 424/45 |

OTHER PUBLICATIONS

Durgs: Facts and Comparisons, 1994 edition, pp. 965 and 966.*
Physicians Desk Reference on lin, Atrovent Inhalation Solution.*

* cited by examiner

Primary Examiner—Thurman K. Page
Assistant Examiner—Amy E Pulliam
(74) Attorney, Agent, or Firm—Robert P. Raymond; Alan R. Stempel; Mary-Ellen M. Devlin

(57) ABSTRACT

On account of the surprisingly powerful and long-lasting effect thereof, the salts of the L-(−)-enantiomer of (endo, syn)-(−)-3-(3-hydroxy-1-oxo-2-phenylpropoxy)-8-methyl-8-(methylethyl)-8-azoniabicyclo [3,2,1]octane are suitable as active substances for drugs administered by inhalation for respiratory tract therapy.

9 Claims, 1 Drawing Sheet

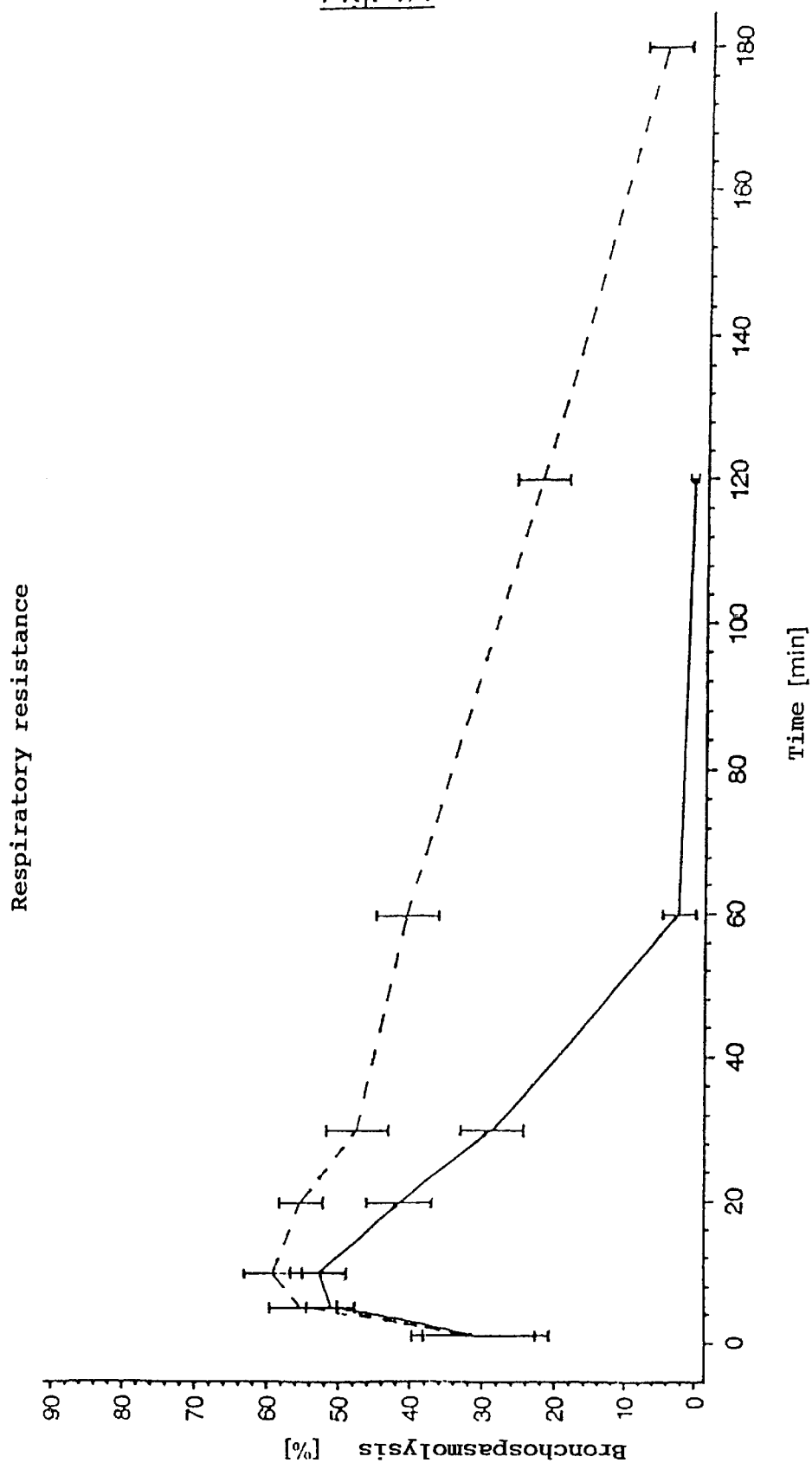

IPRATROPIUM BROMIDE ENANTIOMER WITH PROLONGED DURATION OF EFFECT

This application is a continuation of U.S. application Ser. No. 08/983,420, filed Jan., 14, 1998, now abandoned which claims priority to and is a 371 International Application No. PCT/EP96/03364, filed Jul. 31, 1996.

The invention relates to the use, by inhalation, of (endo, syn)-(−)-3-(3-hydroxy-l-oxo-2-phenylpropoxy)-8-methyl-8-(1-methylethyl)-8-azoniabicyclo [3,2,1]octane salts as bronchospasmolytics with a powerful and particularly long-lasting effect and the use of the salts in the manufacture of asthma preparations.

The racemate of the above-mentioned compound (in the form of the bromide) is on sale under the name Ipratropium bromide as an active substance in anticholinergic drugs.

It has now been found, surprisingly, that the conditions of activity of the racemate, laevorotatory and dextrorotatory enantiomers are significantly different and have major peculiarities which differ substantially from the norm. The eutomer (i.e. the enantiomer having the desired or sought activity) is the L-(−)-enantiomer. Receptor binding studies on CHO-HM receptors have shown that the L-(−)-enantiomer has approximately twice as high an affinity as the racemate. This ratio corresponds to observations which have frequently been made when comparing the effects of enantiomers and racemates.

However, what is surprising in the present case is that administration by inhalation to the (anaesthetised) dog in a comparison of the eutomer with the racemate in the weight ratio 1:2 exhibits not only a higher potency but also a considerably longer duration of activity.

BRIEF DESCRIPTION OF THE DRAWING

The diagram shown in FIG. 1 gives the percentage inhibition of bronchospasm as a function of time. The dotted line (curve B) represents the pattern for the (endo, syn)-(−)-3-(3-hydroxy-l-oxo-2-phenylpropoxy)-8-methyl-8-(1-methylethyl)-8-azoniabicyclo [3,2,1]octane and the continuous line (curve A) gives the pattern for the corresponding racemate, the hydrobromides having been used. 5 μg of the pure L-(−)-enantiomer and, accordingly, 10 μg of the racemate were administered. The experiment was carried out on five test animals using the pure L-enantiomer (BIIH 150 BR) whilst the racemate was administered to seven test animals.

FIG. 1 shows that the inhibition of acetylcholine-induced bronchospasm in the dog by the administration of the Ipratropium bromide aerosol (curve A) has reached a peak of about 55% after about 10 minutes and has fallen back to its initial level after 60 minutes. The same quantity of eutomer (curve B), as contained in the racemate, achieves a 60% inhibition after about 10 minutes and does not fall back to its starting level for 180 minutes.

The half-lives measured show that the eutomer BIIH 150 BR has a duration of activity which is approximately three times longer.

The eutomer is obtained in substantially pure form from the racemate by combined application of high pressure liquid chromatography and recrystallisation. The term "eutomer" for the purposes of the present invention also includes strongly concentrated products (over about 90%), preferably containing more than 95, and particularly more than 97% of the L-(−)-enantiomer. The anion corresponds to the one in the starting compound. If desired, an exchange may be carried out.

The Example which follows is intended to illustrate the preparation of the L-(−)- and D-(+)-enantiomer:

18 grams of Ipratropium bromide are separated by high-pressure liquid chromatography over a Chiralcel OD column (250×20 mm) with a mobile phase composed of 600 hexane, 250 methanol, 150 ethanol and 1 saturated alcoholic NaBr solution (V:V:V:V, throughflow rate 6 ml/min., wavelength 254 nm; sensitivity 0.5 A.U.F.S, solution containing 1 g Ipratropium bromide/5 ml ethanol +5 ml mobile phase +2.5 ml conc. acetic acid).

By repeated chromatography and recrystallisation from ethanol, the L-(−)-enantiomer, white crystals, m.p. 239–40° C. (decomp.), specific rotation $[\alpha]_D^{20}$=−24.06° (c=1.014; $H_2O$), enantiomeric purity 97.4% (HPLC) and the D-(+)-enantiomer, white crystals, m.p. 238–39° C. (decomp.), specific rotation $[\alpha]_D^{20}$=+24.26°(c=1.018; $H_2O$), enantiomeric purity 98.9% (HPLC), are obtained. Elemental analyses and spectra indicate that these compounds are present.

The L-(−)-eutomer in the form of the various salts is suitable, by virtue of being an anticholinergic, for treating chronic obstructive bronchitis and asthma by inhalation, whilst side effects are largely excluded.

For use, the active substance is processed with known excipients and/or carriers to form conventional galenic preparations, e.g. solutions for inhalation, suspensions in liquefied propellant gases, preparations containing liposomes or proliposomes, powders for inhalation (optionally in capsules) for use in conventional inhalers.

Examples of formulations (amounts given in percent by weight):

1. Metering Aerosols

| | |
|---|---|
| Active substance according to the invention | 0.005 |
| Sorbitan trioleate | 0.1 |
| Monofluorotrichloromethane and difluorodichloromethane 2:3 | ad 100 |

The suspension is transferred into a conventional aerosol container with metering valve. 50 μl of suspension, for example, are released on each actuation. If desired, the active substance may also be present in higher doses (e.g. 0.02 wt.-%).

Instead of the chlorinated propellant gases, alternative propellant gases such as TG 134a (1,1,1,2-tetrafluoroethane) and/or TG 227 (1,1,1,2,3,3,3-heptafluoropropane) may also be used.

2. Powder for Inhalation

Micronised powdered active substance (particle size 0.5 to 7 μm) is mixed with micronised lactose and packed into hard gelatine capsules, optionally with other additives. For example, 0.01 mg of active substance and 5 mg of lactose are packed into each capsule. The powder may be inhaled using conventional inhalers, e.g. as in DE-A 3345772.

3. Solutions for Inhalation

Aqueous solutions of the active substance may also be used, the aerosol being produced, for example, by a device according to W091/14468. 0.005 mg of active substance may be administered per spray dose, for example.

The active substance which may be used according to the invention may advantageously also be used in conjunction with other active substances for respiratory tract therapy. $\beta_2$-mimetics may be mentioned in particular; these are used in combinations with 50–100% of the dose for individual use.

The following may be mentioned:

Bambuterol

Bitolterol

Carbuterol
Clenbuterol
Fenoterol
Formoterol
Hexoprenaline
Ibuterol
Pirbuterol
Procaterol
Reproterol
Salbutamol
Salmeterol
Sulfonterol
Terbutaline
Tulobuterol
1-(2-fluoro-4-hydroxyphenyl)-2-[4-(1-benzimidazolyl)-2-methyl-2-butylamino]ethanol
erythro-5'-hydroxy-8'-(1-hydroxy-2-isopropylaminobutyl)-2H-1,4-benzoxazin-3-(4H)-one
1-(4-amino-3-chloro-5-trifluoromethylphenyl)-2-tert.-butylamino)ethanol
1-(4-ethoxycarbonylamino-3-cyano-5-fluorophenyl)-2-(tert.-butylamino)ethanol.

Inhalable steroids such as Budesonide, Beclomethasone (or the 17,21-dipropionate), dexamethasone-21-isonicotinate, Flunisolide and antiallergics such as disodium cromoglycate, Nedocromil, Epinastine may also be used as ingredients in the combination. These combination ingredients may also be administered in the same or smaller doses than when they are used on their own.

What is claimed is:

1. In a method for inhibiting acetycholine induced bronchospasm in a human or an animal which comprises the aerosol administration of inhalable ipratropium bromide, the improvement which comprises the ipratropium bromide being at least about 90% L-(−) ipratropium bromide and the remainder of the ipratropium bromide is D-(+) ipratropium bromide.

2. The method as recited in claim 1 wherein the ipratropium bromide comprises about 95% L-(−)ipratropium bromide.

3. The method as recited in claim 1 wherein the ipratropium bromide comprises about 97% L-(−)-ipratropium bromide.

4. The method as recited in claim 1 further comprising administration of a $\beta_2$-mimetic, an inhalable steroid, an inhalable anti-allergic agent or a combination of such.

5. The method as recited in claim 4 wherein the $\beta_2$-mimetic is bambuterol, bitolterol, carbuterol, clenbuterol, fenoterol, formoterol, hexoprenaline, ibuterol, pirbuterol, procaterol, reproterol, salbutamol, salmeterol, sulfonterol, terbutaline, tulobuterol, 1-(2-fluoro-4-hydroxyphenyl)-2-[4-(1-benzimidazolyl)-2-methyl-2-butylamino]ethanol,
erythro-5'-hydroxy-8'-(1-hydroxy-2-isopropylaminobutyl)-2H-1,4-benzoxazin-3-(4H) -one,
1-(4-amino-3-chloro-5-trifluoromethylphenyl)-2-tert.-butylamino)ethanol, or
1-(4-ethoxycarbonylamino-3-cyano-5-fluorophenyl)-2-(tert.-butylamino)ethanol.

6. The method as recited in claim 4 wherein the inhalable steroid is budesonide, beclomethasone (or the 17,21-diproprionate), dexamethasone-21-isonicotinate, or flunisolide.

7. The method as recited in claim 4 wherein the anti-allergic agent is disodium cromoglycate, nedocromil or epinastine.

8. The method as recited in claim 1 wherein the inhalable ipratropium bromide is formed from a powder.

9. The method as recited in claim 1 wherein the inhalable ipratropium bromide is formed from a liquid solution.

* * * * *